United States Patent [19]

Auth

[11] Patent Number: 4,990,134
[45] Date of Patent: Feb. 5, 1991

[54] TRANSLUMINAL MICRODISSECTION DEVICE

[75] Inventor: David C. Auth, Redmond, Wash.

[73] Assignee: Heart Technology, Inc., Bellevue, Wash.

[21] Appl. No.: 378,741

Related U.S. Application Data

[63] Continuation of Ser. No. 929,956, Nov. 12, 1986, abandoned, which is a continuation-in-part of Ser. No. 816,190, Jan. 6, 1986, abandoned.

[22] Filed: Jul. 11, 1989

[51] Int. Cl.$^5$ .............................................. A61B 17/20
[52] U.S. Cl. ...................................................... 604/22
[58] Field of Search ................. 604/22, 155, 156, 158; 433/125, 142, 166

[56] References Cited

U.S. PATENT DOCUMENTS

| | | | |
|---|---|---|---|
| 3,309,772 | 3/1967 | Lieb et al. ............................ | 433/166 |
| 3,809,093 | 5/1984 | Abraham . | |
| 3,892,117 | 7/1975 | Nelson ................................. | 433/165 |
| 3,937,222 | 2/1976 | Banko .................................. | 128/305 |
| 4,264,307 | 4/1981 | Neuwirth . | |
| 4,445,509 | 5/1984 | Auth ..................................... | 128/752 |
| 4,591,355 | 5/1986 | Hike ...................................... | 128/305 |

FOREIGN PATENT DOCUMENTS 117519  2/1984  European Pat. Off. .

OTHER PUBLICATIONS

Catalog Cut, Teledyne Densco, Denver, Colo. 80207, 11/83.

Primary Examiner—David J. Isabella
Attorney, Agent, or Firm—Kane, Dalsimer, Sullivan, Kurucz, Levy, Eisele and Richard

[57] ABSTRACT

An abrasive tipped rotating cutting tool for use in removing abnormal deposits within a patient's vessels is described. The tip is preferably covered with a material such as diamond grit, and rotated at high speed to pulverize any abnormal deposits contained within the vessel.

In a preferred embodiment of the invention, the tip is ellipsoidal in shape, and the coarseness of the abrasive material on the tip is varied from most coarse adjacent the distal end of the tip to finest adjacent the portion of the tip which has the widest diameter. Preferably, there is no abrasive on the widest part of the tip in order to prevent the tip from injuring a patient's vessel in the event that the tip is allowed to remain in one place for an extended period of time. In addition, there may be radial openings formed in the tip which permit water to be pumped therethrough in order to act as a lubricant for assisting in the cutting action of the tip.

The invention may use either an autraumatic tip or a preformable guide wire to guide the cutting tip through a patient's vessel.

13 Claims, 2 Drawing Sheets

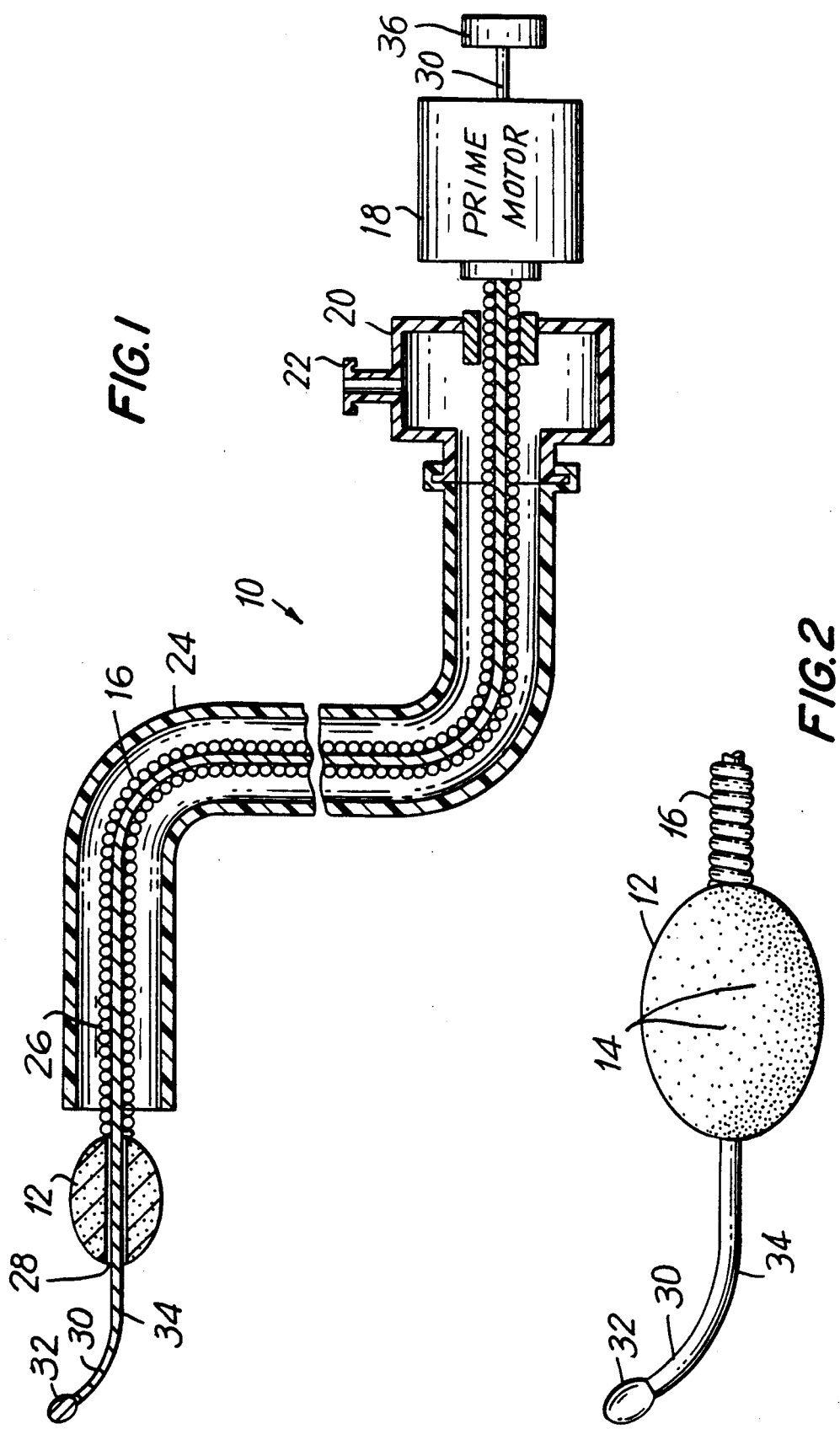

TRANSLUMINAL MICRODISSECTION DEVICE

CROSS-REFERENCE TO RELATED APPLICATIONS

The present application is a continuation of U.S. patent application Ser. No. 929,956, filed Nov. 12, 1986, now abandoned, which in turn is a continuation-in-part of U.S. patent application Ser. No. 816,190, filed Jan. 6, 1986, now abandoned.

BACKGROUND OF THE INVENTION

The present invention relates to a mechanical device which is used in medical applications and which is capable of differentially cutting abnormal deposits from within a patient's vessels.

U.S. Pat. No. 4,445,509 entitled METHOD AND APPARATUS FOR REMOVAL OF ENCLOSED ABNORMAL DEPOSITS which issued to David C. Auth on May 1, 1984 describes a rotary mechanical system for differentially cutting relatively hard intravascular deposits while sparing relatively soft, normal tissue. In the device described in that patent, a hollow channel was used for suction removal of debris generated during the cutting process in order to prevent the debris from acting as the nucleus for thrombogenesis or from occluding smaller vascular channels and thereby inhibiting the normal flow of life sustaining blood.

Suctioning of debris may not recover all of the cutting products if vascular flow is present in the artery being treated, since fluid motion at the cutting tip will immediately carry some debris downstream. U.S. Pat. No. 4,207,874 entitled LASER TUNNELLING DEVICE which issued to D. S. Choy on June 17, 1980 describes an apparatus which removes intravascular deposits by using a laser to vaporize intravascular obstructions. When laser energy is used to vaporize debris, the laser may provide sufficient energy to release each constituent molecule from the host lattice or it may produce gaseous products within the solid matrix, thereby causing a rupture of the matrix and the release of smaller constituent particles of the mass. In the former case, the amount of energy required to uncouple each individual molecule is relatively large due to the binding energy of each molecule and to the large number of molecules per unit volume of obstructing mass. In the latter case, the released particles can be relatively large and may be capable of obstructing smaller vascular branches distal to the site of the treated obstruction.

In U.S. Pat. No. 4,445,509, referred to above, the preferential cutting of hard deposits vis-a-vis soft normal tissue is a desirable feature. Unfortunately, harmful obstructing deposits can, on occasion, be soft. Frequently, such soft occluding deposits are also lacking in physical toughness, i.e., they lack the ability to recover after deformation. Muscular tissue tends to be rather tough and to be able to recover after significant elastic deformation. Thus, an additional physical property which may be considered for differentiating the cutting efficacy of a particular device is its ability to distinguish between soft (compliant), tough tissue, which will not break up as a result of local deformation, and soft, weak tissue, which will break up under local deformation. As taught in U.S. Pat. No. 4,445,509, the differential cutting action derives from the ability of soft tissue to "dive" out of the way before it is caught in front of the cutting edge and cleaved off. The process of "diving" implies deformation which can decimate soft, weak tissue without seriously damaging soft, tough tissue. However, even soft, tough tissue can be cleaved if the rate at which the deformation required to escape cleavage exceeds the speed with which the tissue can move given its own inertia. Thus, increasing the surface speed of the cutting edge can eventually result in the ability to cleave soft, tough tissue. This distinction can be useful when it is desirable to cleave obstructive tissue masses which are soft and weak or soft and tough. Depending upon the local vessel anatomy, some damage to normal vessel endothelium or media may occur, and although less than desirable, that may well be a price worth paying to relieve the underlying obstructive condition. Since damage to endothelium and media occurs routinely in surgical vessel grafts which subsequently re-endothelize, the prognosis for rehealing of intima and media damaged adjacent to removed pathological material is good. Administration of drugs which suppress normal clotting may be required to inhibit thrombosis at the damage site during and after treatment.

When intravascular obstructions have a fibrous structure, there is a tendency to turn up a "scab" of material at the base of the cutting zone. Such scabs grow in size with additional cutting rather than being clipped off. They can present a problem if left within the artery, as they may flop across the arterial vessel and obstruct flow or they may become a nucleating site for thrombogenesis or regrowth of atheroma.

SUMMARY OF THE INVENTION

It has been found that tiny cutting surfaces which act as shovels operating at surface speeds of about 40 feet per second (ft/sec) can snip off microscopic divots before a scab can grow to appreciable size. These tiny shovels are preferrably comprised of fragments of diamond crystal or grit. Other sharp grit could be used, but diamond is inexpensive in this format and provides good wear characteristics. When these crystalline fragments (shovels) are very small in size, they necessarily generate very small debris fragments. If the debris tissue fragments are sufficiently small in size, they will propagate through the tiniest vascular channels (capillary beds) without clogging them. Thus, when using 30 micron size diamond fragments, the chip size of the fragments can easily be less than 5 microns, i.e., less than the size of a red blood cell, which, of course, propagates through the capillary network. A 5 micron size debris fragment contains many millions of constituent molecules. Accordingly, the energy required to produce such fragments is orders of magnitude less than would be required if a laser using molecular evaporation was employed. Releasing many calories of energy within a blood vessel (using a laser) carries an attendant high risk of vessel wall damage by thermal conduction and subsequent thermal necrosis.

In accordance with the present invention, an elliposoidal cutting head, or burr, similar in shape to that depicted in U.S. Pat. No. 4,445,509 is coated with tiny diamond chips (shovels). The cutting head is rotated at a speed which, in conjunction with its geometrical circumference, provides a surface velocity of approximately 40 ft/sec. It has been found that a tip of this type, operated at such a tip velocity, is able to cut soft material at a high removal rate, while generating microscopic particles (on the order of 5 microns or less) and leaving behind a tissue base having a smooth appearance. Such tips can now be fabricated in sizes ranging from about 0.5 mm in diameter up to 6 mm diameter. To achieve a surface speed of 40 ft/sec with a tip of 1.5 mm diameter requires a rotation rate of approximately 155,000 revolutions per minute (rpm).

Transmission of such high rates of rotation through a flexible catheter has recently been shown to be possible using a 0.020" trifilar helically wound drive shaft spinning within a thin plastic tube using a solid steel shaft having a 0.009" diameter, which tapers down to less than 0.005" at the tip, as a stationary core or rail. Infusion of biocompatible saline through the plastic sheath provides cooling of the sliding interface during operation.

Using the same mechanical configuration but operating at reduced rpm allows the same device to preferentially cut hard material while sparing soft material. Operation at high rotation speed will, of course, cut hard material very well. Indeed, hard material is usually removed more easily at all speeds relative to soft material. The point is that at very high surface speeds (approximately 40 ft/sec and above) even the soft tissue can be cut, whereas at lower speeds it is very difficult to remove, but the hard material can still be dissected. Thus, a single device whose speed is modulated becomes a multipurpose device capable of differential cutting or soft tissue cutting. This device has now been shown to work in a variety of animal tissues varying from soft to hard while being flexibly conveyed through a plastic catheter.

In a preferred embodiment of the invention, the burr is coated with coarse abrasive material at its distal end and with finer abrasive material at distances more remote from the distal end, such that the coarse material acts to quickly abrade obstructions as the burr is advanced, the finer abrasive material being adapted more toward polishing the inner surfaces of the vessel. It is preferable that in the region of the burr having the widest diameter there be essentially no abrasive material in order to prevent a rotating burr which is not being advanced through a vessel from abrading through the sides of the vessel.

BRIEF DESCRIPTION OF THE DRAWING

In the Drawing:

FIG. 1 depicts a preferred embodiment of the present invention;

FIG. 2 is an exploded side view of the tip of the device of FIG. 1;

DETAILED DESCRIPTION OF THE PREFERRED EMBODIMENT

Figure 3:
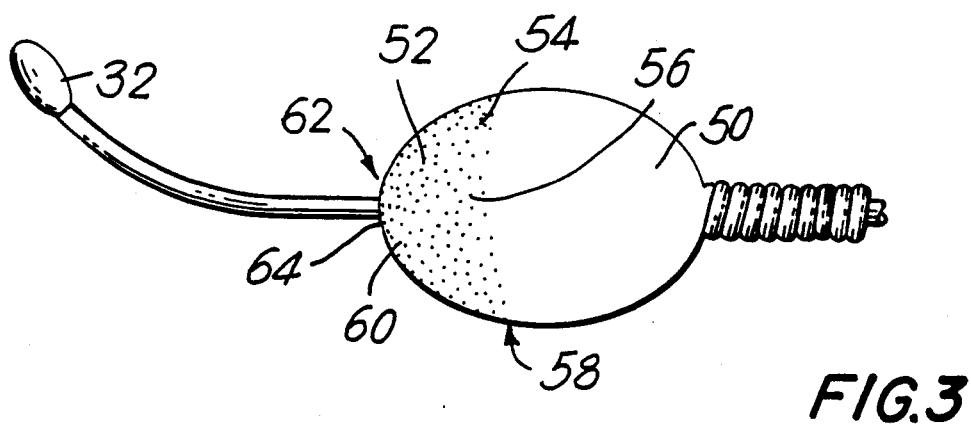
FIG. 3 is a side view of a version of the embodiment of the invention which includes a variable grit angioplasty burr.

Referring generally to FIGS. 1 and 2, the preferred embodiment 10 of the present invention is shown. The invention 10 comprises an abrasive tip 12 and an atraumatic tip 32 which is generally of the type described in U.S. patent application Ser. No. 649,089 entitled TRANSLUMINAL THROMBECTOMY APPARATUS, filed Sept. 10, 1984 by the present inventor which is steerable for accessing branch vessels. The tip 12 is covered with an abrasive cutting material, such as diamond grit 14, which is used in the preferred embodiment of the invention. The tip 12 is connected via a hollow, flexible drive shaft 16 to a variable speed prime mover 18. In the preferred embodiment of the invention, the drive shaft 16 is a 0.020" diameter trifilar helically wound drive shaft. The drive shaft 16 is sealably coupled to a variable speed rotational prime mover 18, which is capable of high speed rotation. The coupling is accomplished using a sealed chamber 20 having an injection port 22, so that injection of drugs or fluids into the lumen which is formed between the drive shaft 16 and a surrounding plastic sheath can be accommodated. The distal segment 26 of the flexible shaft 16 is preferably passivated with a coating, of a low-friction material, such as du Pont's Teflon brand tetrafluoroethylene homopolymer, which will inhibit the winding of intravascular fiber on the shaft 16 during rotation. The tip 12 includes a central bore 28 which is aligned with the opening which extends down the length of the hollow shaft 16. The tip 12 and the shaft 16 are routed into a vessel by using a central guide rail 30, which may be comprised of a 0.005" diameter steel wire. Adjacent the blunt tip 32 at the distal end of the guide rail 30, there is a preformable portion 34 of the guide rail 30 which the physician using the invention may bend to facilitate directing the invention into branch vessels. The guide rail 30 extends completely through the shaft 16 and through the prime mover 18 to a rotatable knob 36 which permits the guide rail 30 to be rotated in order to direct the tip 32 through a patient's vessel in order to perform a thrombectomy as described in U.S. patent application Ser. No. 649,101. The drive shaft 16 and the central rail 30 may be individually moved with respect to each other and with respect to the plastic sheath 24 in order to engage a thrombus or an atheromatous occlusion. The rotational prime mover 18 for the high-speed helical drive shaft 16 is preferably operable in a range of from 20,000 rpm to greater than 155,000 rpm. The size of the burr tip 12 is typically in a range of from less than 1 mm diameter up to about 6 mm, depending upon the vessel size desired where the lesion is being recanalized.

Such a device provides for transluminal recanalization of intravascular lesions of soft or hard constitution consisting of thrombotic or atheromatous material.

Referring to FIG. 3, a modified version of the present invention utilizes a burr 50 having coated on the distal surface thereof, i.e., the portion most remote from the prime mover 18 (shown in FIG. 1), a variety of particles 52 ranging in size from about 30 microns up to about 150 microns in diameter. The smaller particles 56 are preferably located in the area 54 adjacent to the portion 58 of the burr 50 having the largest diameter, and the larger particles 60 are preferably located in the area 62 adjacent to the distal end 64 of the burr 50. Accordingly, when the burr 50 is inserted into a patient's vessel the larger particles 60 adjacent the distal end 64 serve to quickly abrade through any lodged material, thereby opening the vessel rapidly. The smaller particles 56 continue to abrade and polish the inner surface of the vessel as the burr 50 is advanced therethrough. The region 58 having the widest diameter is preferably substantially devoid of abrasive particles, so that it acts as a central bearing area. Accordingly, if the burr 50 is allowed to remain in a particular position within a patient's vessel, the absence of abrasive material in the central region 58 prevents that region from abrading through the wall of the patient's vessel.

Figure 4:
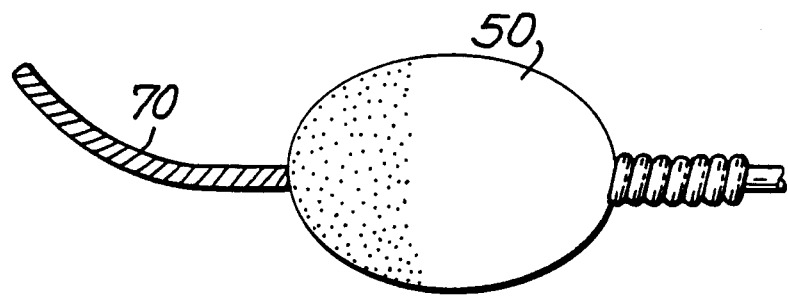
FIG. 4 is a side view of the embodiment of FIG. 3 in which the atraumatic tip of FIG. 3 is replaced by a preformable guide wire.

Referring to FIG. 4 the atraumatic tip 32 illustrated in FIGS. 1–3 can be replaced by preformable spring tip 70 of a type used in the catheter art. The preformable spring tip 70 can be bent by a physician, as desired, prior to insertion into a patient's vessel, in order that the unit may be guided through a patient's vessel to a particular location, generally under the assistance of fluoroscopy.

Figure 5:
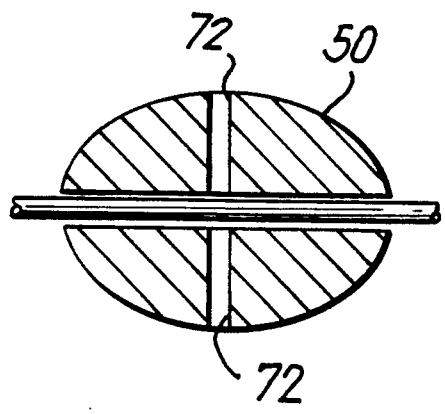
FIG. 5 is a cross-sectional view of an embodiment including radial water spouts.

Referring generally to FIG. 5, radial openings 72 may be formed in the burr 50 to permit the outward flow of water (pumped in from the proximal end), whereby a friction reducing bearing will be accomplished.

I claim:

1. A transluminal microdissection device comprising:
   (a) flexible, hollow drive shaft having a rotatable, substantially elliposoidal cutting tip attached thereto, said tip having a diameter which is greater than that of said drive shaft and said tip having a substantially cylindrical opening in fluid communication with said hollow drive shaft so that said drive shaft and tip can be guided along a guide wire;
   (b) an abrasive surface on said tip, said abrasive surface being comprised of abrasive material attached to the surface of said tip; and
   (c) a rotatable prime mover which is capable of rotating said drive shaft at a rotation rate of from about 20,000 revolutions per minute to about 160,000 revolutions per minute, whereby said abrasive material microdissects particles small enough to pass through the capillaries of a person.

2. The transluminal microdissection device of claim 1 further comprising a tubular sheath which surrounds said flexible drive shaft and chamber means for sealably attaching to said tubular sheath, said chamber means including a seal through which said drive shaft passes.

3. The transluminal microdissection device of claim 1 wherein said abrasive material covers only the distal surface of said tip.

4. The transluminal microdissection device of claim 1 wherein the coarseness of said abrasive material is varied from finest to most coarse, with the most coarse abrasive material adjacent the distal end of said tip and the finest abrasive material closest to the portion of said tip having the widest diameter.

5. The transluminal microdissection device of claim 4 wherein said abrasive material does not cover the surface of said tip where said tip has its widest diameter.

6. The transluminal microdissection device of claim 5 wherein said abrasive material does not cover the surface of said tip between the proximal end of said tip and the portion of said tip which has its widest diameter.

7. The transluminal microdissection device of claim 1 wherein said rotatable cutting tip is not fluted.

8. The transluminal microdissection device of claim 1 further comprising a tubular sheath which surrounds said flexible drive shaft and chamber means for sealably attaching to said tubular sheath, said chamber means including a seal through which said drive shaft passes.

9. A transluminal microdissection device comprising:
   (a) a flexible, hollow drive shaft having a rotatable, substantially elliposoidal cutting tip attached thereto, said tip having a diameter which is greater than that of said drive shaft and said tip having a substantially cylindrical opening in fluid communication with said hollow drive shaft so that said drive shaft and tip can be guided along a guide wire;
   (b) an abrasive surface on said tip, said abrasive surface being comprised of abrasive material attached to the surface of said tip;
   (c) a rotatable prime mover which is capable of rotating said drive shaft at a rotation rate of from about 20,000 revolutions per minute to about 160,000 revolutions per minute, whereby said abrasive material microdissects particles small enough to pass through the capillaries of a person;
   (d) a tubular sheath which surrounds said flexible drive shaft and forms a lumen between said drive shaft and said sheath; and
   (e) a chamber means for sealably attaching to said tubular sheath and communicating with said lumen, said chamber means including a seal through which said drive shaft passes and a port which extends into said chamber means wherein said lumen is accessible through said port.

10. A transluminal microdissection device comprising:
    (a) a flexible drive shaft having a rotatable, substantially ellipsoidal cutting tip attached thereto, said tip having a diameter which is greater than that of said drive shaft;
    (b) an abrasive surface on said tip, said abrasive surface being comprised of abrasive material attached to the distal surface of said tip, the abrasive material adjacent the distal end of said tip being more coarse then abrasive material closer to the portion of said tip where said tip has its widest diameter; and
    (c) a rotatable prime mover which is capable of rotating said drive shaft at a rotation rate of from about 20,000 revolutions per minute to about 160,000 revolutions per minute, whereby said abrasive material microdissects particles small enough to pass through the capillaries of a person.

11. The device of claim 1 wherein the abrasive material comprises diamond chips having a largest dimension of substantially 30 microns or smaller.

12. The device of claim 7 wherein the abrasive material comprises diamond chips having a largest dimension of substantially 30 microns or smaller.

13. A transluminal microdissection device comprising:
    (a) a guide wire;
    (b) a flexible, hollow drive shaft having a rotatable, substantially ellipsoidal cutting tip attached thereto, said tip having a diameter which is greater than that of said drive shaft and said tip having a substantially cylindrical opening in fluid communication with said hollow drive shaft so that said drive shaft and tip can be guided along a guide wire;
    (c) an abrasive surface on said tip, said abrasive surface being comprised of abrasive material attached to the surface of said tip; and
    (d) a rotatable prime mover which is capable of rotating said drive shaft at a rotation rate of from about 20,000 revolutions per minute to about 160,000 revolutions per minute, whereby said abrasive material microdissects particles small enough to pass through the capillaries of a person.

* * * * *

REEXAMINATION CERTIFICATE (3046th)

United States Patent [19]
Auth

[11] B1 4,990,134
[45] Certificate Issued Nov. 5, 1996

[54] TRANSLUMINAL MICRODISSECTION DEVICE

[75] Inventor: David C. Auth, Redmond, Wash.

[73] Assignee: Heart Technology, Inc., Redmond, Wash.

Reexamination Request:
No. 90/003,699, Jan. 23, 1995

Reexamination Certificate for:
Patent No.: 4,990,134
Issued: Feb. 5, 1991
Appl. No.: 378,741
Filed: Jul. 11, 1989

Related U.S. Application Data

[63] Continuation of Ser. No. 929,956, Nov. 12, 1986, abandoned, which is a continuation-in-part of Ser. No. 816,190, Jan. 6, 1986, abandoned.

[51] Int. Cl.$^6$ .................................................. A61B 17/20
[52] U.S. Cl. ................................................................ 604/22
[58] Field of Search ........................... 604/22, 155, 156, 604/158; 433/125, 142, 166

[56] References Cited

U.S. PATENT DOCUMENTS

| | | |
|---|---|---|
| 3,614,953 | 10/1971 | Moss . |
| 4,002,169 | 1/1977 | Cupler, II . |
| 4,465,072 | 8/1984 | Taheri . |
| 4,591,355 | 5/1985 | Hilse . |
| 4,622,503 | 11/1986 | Sundblom et al. . |
| 4,669,465 | 6/1987 | Moore et al. . |

FOREIGN PATENT DOCUMENTS

163502 12/1985 European Pat. Off. .

*Primary Examiner*—David J. Isabella

[57] ABSTRACT

An abrasive tipped rotating cutting tool for use in removing abnormal deposits within a patient's vessels is described. The tip is preferably covered with a material such as diamond grit, and rotated at high speed to pulverize any abnormal deposits contained within the vessel.

In a preferred embodiment of the invention, the tip is ellipsoidal in shape, and the coarseness of the abrasive material on the tip is varied from most coarse adjacent the distal end of the tip to finest adjacent the portion of the tip which has the widest diameter. Preferably, there is no abrasive on the widest part of the tip in order to prevent the tip from injuring a patient's vessel in the event that the tip is allowed to remain in one place for an extended period of time. In addition, there may be radial openings formed in the tip which permit water to be pumped therethrough in order to act as a lubricant for assisting in the cutting action of the tip.

The invention may use either an autraumatic tip or a preformable guide wire to guide the cutting tip through a patient's vessel.

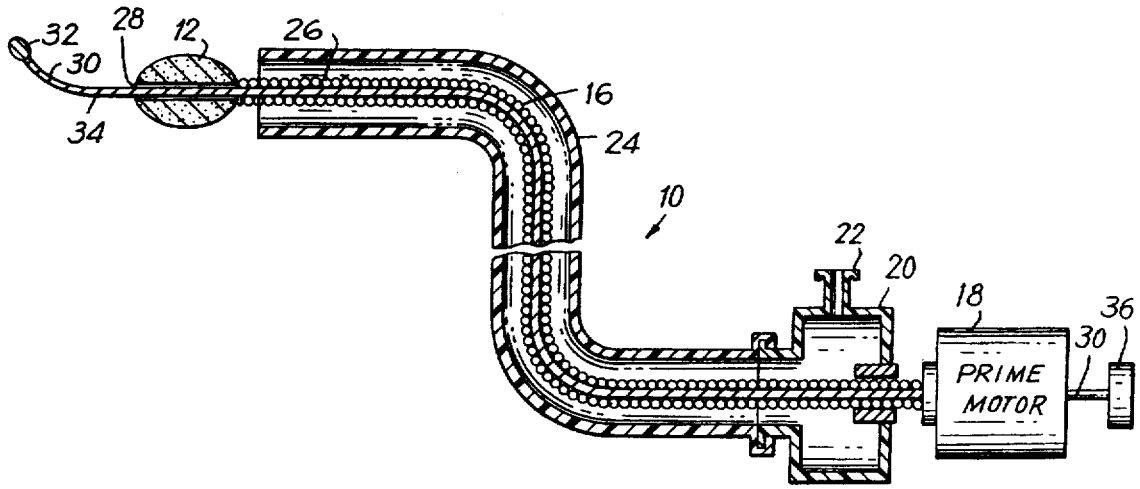

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–7, 9–13 is confirmed.

Claim 8 is determined to be patentable as amended.

8. The transluminal microdissection device of claim [1] *10* further comprising a tubular sheath which surrounds said flexible drive shaft and chamber means for sealably attaching to said tubular sheath, said chamber means including a seal through which said drive shaft passes.

* * * * *